United States Patent

Müller et al.

[11] Patent Number: 6,166,058
[45] Date of Patent: Dec. 26, 2000

[54] FUNGICIDAL MIXTURES

[75] Inventors: Bernd Müller, Frankenthal; Hubert Sauter, Mannheim; Eberhard Ammermann, Heppenheim; Gisela Lorenz, Hambach; Siegfried Strathmann, Limburgerhof; Klaus Schelberger, Gönnheim; Maria Scherer, Landau; Manfred Hampel, Neustadt; Reinhold Saur, Böhl-Iggelheim; Joachim Leyendecker, Ladenburg, all of Germany

[73] Assignee: BASF Aktiengesellschaft, Ludwigshaften, Germany

[21] Appl. No.: 09/214,507

[22] PCT Filed: Jun. 27, 1997

[86] PCT No.: PCT/EP97/03378

§ 371 Date: Jan. 7, 1999

§ 102(e) Date: Jan. 7, 1999

[87] PCT Pub. No.: WO98/01033

PCT Pub. Date: Jan. 15, 1998

[30] Foreign Application Priority Data

Jul. 10, 1996 [DE] Germany .................. 196 27 696
Aug. 30, 1996 [DE] Germany .................. 196 35 081

[51] Int. Cl.[7] .......... A01N 43/56; A01N 43/64; A01N 37/12; A01N 37/44; A01N 37/52
[52] U.S. Cl. .......... 514/383; 514/407; 514/539; 514/634
[58] Field of Search .................. 514/383, 407, 514/539, 634

[56] References Cited

U.S. PATENT DOCUMENTS 4,783,475 11/1988 Wiedmer .................. 514/383

FOREIGN PATENT DOCUMENTS

| 0253213 | 1/1988 | European Pat. Off. |
| 0741970 | 11/1996 | European Pat. Off. |
| 96/01256 | 1/1996 | WIPO |
| 96/01258 | 1/1996 | WIPO |

OTHER PUBLICATIONS

Tomlin, The Pesticide Manual Incorporating the Agrochemicals Handbook, 10th Ed. (1995) pp. 593 & 594.
Database WPI, Section Ch. Week 8938, Derwent Publications, AN 89–273349 (English abstract of JP 0 97 415, Aug. 9, 1989.

*Primary Examiner*—Allen J. Robinson
*Attorney, Agent, or Firm*—Keil & Weinkauf

[57] ABSTRACT

Fungicidal mixture comprising, as active components, $a_1$) the oxime ether carboxylate of the formula Ia

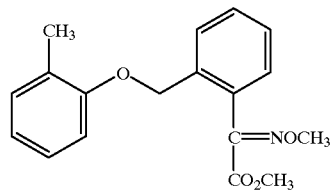

(Ia)

or a salt or adduct thereof, and/or $a_2$) a carbamate of the formula Ib

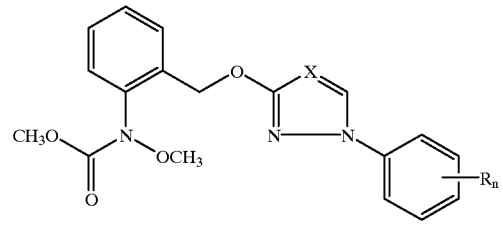

(Ib)

where X is CH or N, n is 0, 1 or 2 and R is halogen, $C_1$–$C_4$-alkyl or $C_1$–$C_4$-haloalkyl, it being possible for the radicals R to be different if n is 2, or a salt or adduct thereof, and b) iminoctadine II $$H_2N\text{—}C(=NH)\text{—}NH\text{—}(CH_2)_8\text{—}NH\text{—}(CH_2)_8\text{—}NH\text{—}C(=NH)\text{—}NH_2 \quad (II)$$

or a salt or adduct thereof, in a synergistically active amount, and its use for controlling harmful fungi.

17 Claims, No Drawings

FUNGICIDAL MIXTURES

This application is 371 of PCT/EP97/03378, filed Jun. 27, 1997.

The present invention relates to a synergistic fungicidal mixture which comprises, as active components, $a_1$) the oxime ether carboxylate of the formula Ia

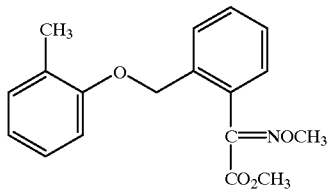

(Ia)

or a salt or adduct thereof, and/or $a_2$) a carbamate of the formula Ib

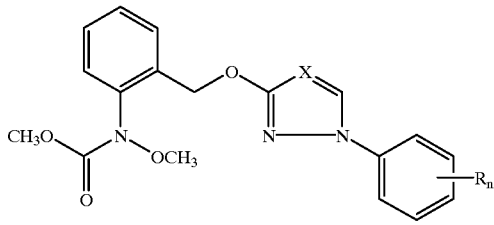

(Ib)

where x is CH or N, n is 0, 1 or 2 and R is halogen, $C_1$–$C_4$-alkyl or $C_1$–$C_4$-haloalkyl, it being possible for the radicals R to be different if n is 2, or a salt or adduct thereof, and b) iminoctadine II $$H_2N\text{---}C(=NH)\text{---}NH\text{---}(CH_2)_8\text{---}NH\text{---}(CH_2)_8\text{---}NH\text{---}C(=NH)\text{---}NH_2 \quad (II)$$

or a salt or adduct thereof,
in a synergistically active amount.

Moreover, the invention relates to methods of controlling harmful fungi with mixtures of the compounds I and II and to the use of the compound I and the compound II for the preparation of such mixtures.

The compound of the formula Ia, its preparation and its action against harmful fungi has been disclosed in EP-A 253 213. WO-A 96/01,256 and WO-A 96/01,258 describe compounds of the formula Ib, their preparation and their use. The compound II (common name: iminoctadine), its preparation and its action against harmful fungi are also known (cf. "Pesticide Manual", page 593).

It was an object of the present invention to provide mixtures which have an improved activity against harmful fungi combined with a reduced total amount of active ingredients applied (synergistic mixtures) with a view to reducing the rates of application and to improving the spectrum of action of the known compounds I and II.

Accordingly, we have found that this object is achieved by the mixture defined at the outset. Moreover, we have found that better control of harmful fungi is possible by applying the compound I and the compound II simultaneously, ie. together or separately, or by applying the compound I and the compound II in succession than when the individual compounds are used alone.

The formula Ib represents, in particular, carbamates in which the combination of the substituents corresponds to one row of the table below:

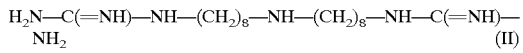

(Ib)

| No. | X | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl, 4-$CH_3$ |
| I.52 | CH | 3-Cl, 4-$CH_3$ |

Compounds I.12, I.23, I.32 and I.38 are particularly preferred.

Due to the basic character of the oxime ether unit, the compounds Ia and Ib are capable of forming salts or adducts with inorganic or organic acids or with metal ions.

Examples of inorganic acids are hydrohalic acids such as hydrofluoric acid, hydrochloric acid, hydrobromic acid and hydroiodic acid, furthermore carbonic acid, sulfuric acid, phosphoric acid and nitric acid.

Suitable organic acids are, for example, formic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of from 1 to 20 carbon atoms), arylsulfonic acids or -disulfonic acids (aromatic radicals such as phenyl and naphthyl which have attached to them one or two sulfo groups), alkylphosphonic acids (phosphonic acids having straight-chain or branched alkyl radicals of from 1 to 20 carbon atoms), arylphosphonic acids or -diphosphonic acids (aromatic radicals such as phenyl and naphthyl which have attached to them one or two phosphonic acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the first to eighth sub-group, in particular chromium, manganese, iron, cobalt, nickel, copper, zinc and others and also of the second main group, especially calcium and magnesium, and of the third and fourth main group, in particular aluminum, tin and lead. The metals can be in the various valences which they can assume.

When preparing the mixtures, it is preferred to employ the pure active ingredients I and II, with which further active ingredients against harmful fungi or other pests such as insects, arachnids or nematodes, or else herbicidal or growth-regulating active ingredients or fertilizers can be admixed.

The mixtures of the compounds I and II, or the simultaneous, joint or separate, use of the compounds I and II, are distinguished by an outstanding activity against a broad spectrum of phytopathogenic fungi, in particular from the classes of the Ascomycetes, Basidiomycetes, Phycomycetes and Deuteromycetes.

Some of them act systemically and can therefore also be employed as foliar- and soil-acting fungicides.

They are especially important for controlling a large number of fungi in a variety of crop plants such as cotton, vegetable species (eg. cucumbers, beans and cucurbits), barley, grass, oats, coffee, maize, fruit species, rice, rye, soybeans, grapevines, wheat, ornamentals, sugar cane, and on a variety of seeds.

They are particularly suitable for controlling the following phytopathogenic fungi: Erysiphe graminis (powdery mildew) on cereals, Erysiphe cichoracearum and Sphaerotheca fuliginea on cucurbits, Podosphaera leucotricha on apples, Uncinula necator on grapevines, Puccinia species on cereals, Rhizoctonia species on cotton, rice and lawns, Ustilago species on cereals and sugar cane, Venturia inaequalis (scab) on apples, Helminthosporium species on cereals, Septoria nodorum on wheat, Botrytis cinerea (gray mold) on strawberries, vegetables, ornamentals and grapevines, Cercospora arachidicola on peanuts, Pseudocercosporella herpotrichoides on wheat and barley, Pyricularia oryzae on rice, Phytophthora infestans on potatoes and tomatoes, Plasmopara viticola on grapevines, Alternaria species on vegetables and fruit, and Fusarium and Verticillium species.

Furthermore, they can be used in the protection of materials (eg. in the protection of wood), for example against Paecilomyces variotii.

The compounds I and II can be applied simultaneously, either together or separately, or in succession, the sequence in the case of separate application generally not having any effect on the result of the control measures.

The compounds I and II are normally used in a weight ratio of from 10:1 to 0.05:2, preferably 5:1 to 0.05:1, in particular 1:1 to 0.05:1. In this regard, the amount of the compounds I relates to Ia or Ib or, if appropriate, a mixture thereof.

The application rates of the mixtures according to the invention are, especially in the case of areas under agricultural crops, from 0.01 to 7 kg/ha, preferably 0.01 to 5 kg/ha, in particular 0.1 to 3.0 kg/ha, depending on the nature of the desired effect.

In the case of the compounds I, the application rates are from 0.01 to 2.5 kg/ha, preferably 0.05 to 2.5 kg/ha, in particular 0.1 to 1.0 kg/ha.

Correspondingly, in the case of the compound II, the application rates are from 0.01 to 10 kg/ha, preferably 0.05 to 5 kg/ha, in particular 0.05 to 2 kg/ha.

For seed treatment, the application rates of the mixture are generally from 0.001 to 250 g/kg seed, preferably 0.01 to 100 g/kg, in particular 0.01 to 50 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated for example in the form of ready-to-spray solutions, powders or suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and salts of sulfated hexa-, hepta- and octadecanols or fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl polyglycol ethers or tributylphenyl polyglycol ether, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, ligninsulfite waste liquors or methylcellulose.

Powders, materials for spreading and dusts can be prepared by mixing or jointly grinding the compounds I or II or the mixture of the compounds I and II with a solid carrier.

Granules (eg. coated granules, impregnated granules or homogeneous granules) are normally prepared by binding the active ingredient, or active ingredients, to a solid carrier.

Fillers or solid carriers are, for example, mineral earths such as silica gel, silicas, silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate, ureas, and products of vegetable origin such as cereal meal, tree bark meal, wood meal and nutshell meal, cellulose powders or other solid carriers.

The formulations generally comprise from 0.1 to 95% by weight, preferably 0.5 to 90% by weight, of one of the compounds I or II, or of the mixture of the compounds I and II. The active ingredients are employed in a purity of from 90% to 100%, preferably 95% to 100% (according to NMR spectrum or HPLC).

Application of the compounds I or II, or the mixtures, or the corresponding formulations, is effected by treating the harmful fungi, their environment, or the plants, seeds, soils, areas, materials or spaces to be kept free from them with a fungicidally active amount of the mixture, or of the compounds I and II in the case of separate application.

Application can be effected before or after infection by the harmful fungi.

USE EXAMPLE

Activity Against *Botrytis Cinerea*

The active ingredients, separately or together, were formulated as a 10% emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols) and diluted with water to give the desired concentration.

Bell pepper seedlings cv. "Neusiedler Ideal Elite" were allowed to develop 4–5 leaves properly and then sprayed to runoff point with aqueous suspensions comprising 80% by weight of active ingredient and 20% by weight of emulsifier in the dry matter. After the spray coating had dried on, the plants were sprayed with a conidia suspension of the fungus Botrytis cinerea and placed into a chamber at 22–24° C. and high atmospheric humidity. After 5 days, the disease on the untreated control plants had developed to such an extent that the foliar necroses formed covered most of the leaves.

Evaluation was carried out by determining the infected leaf areas in percent. These percentages were converted into efficacies. The efficacy (W) was calculated as follows using Abbot's formula:

$$W=(1-\alpha)\cdot 100/\beta$$

$\alpha$ is the fungal infection of the treated plants in % and
$\beta$ is the fungal infection of the untreated (control) plants in %.

An efficacy of 0 means that the infection level of the treated plants corresponds to that of the untreated control plants; an efficacy of 100 means that the treated plants were not infected.

The expected efficacies of the mixtures of the active ingredients were determined using Colby's formula [R. S. Colby, Weeds 15, 20–22 (1967)] and compared with the observed efficacies.

Colby's formula:

$$E=x+y-x\cdot y/100$$

E expected efficacy, expressed in % of the untreated control, when using the mixture of the active ingredients A and B at concentrations of a and b x efficacy, expressed in % of the untreated control, when using active ingredient A at a concentration of a y efficacy, expressed in % of the untreated control, when using active ingredient B at a concentration of b Activity Against *Botrytis Cinerea* (gray mold)

Bell pepper seedlings (cultivar: "Neusiedler Ideal Elite") having 4–5 leaves were sprayed to runoff point with the preparation of the active ingredient. After the plants had dried, they were sprayed with a conidia suspension of the fungus *Botrytis cinerea* and then left for 5 days at 22–24° C. and high atmospheric humidity. Scoring was carried out visually.

We claim:

1. A fungicidal composition comprising, as active components $a_2$) a carbamate Ib (Ib)

where X is CH or N, n is 0, 1 or 2 and R is halogen, $C_1$–$C_4$-alkyl or $C_1$–$C_4$-haloalkyl, it being possible for the radicals R to be different if n is 2, or a salt or adduct thereof, and iminoctadine II (II)

$$H_2N-\underset{\underset{NH}{\|}}{C}-NH-(CH_2)_8-NH-(CH_2)_8-NH-\underset{\underset{NH}{\|}}{C}-NH_2$$

or a salt or adduct thereof,
   in a synergistically effective amount.

2. The composition defined in claim 1 wherein the weight ratio of the carbamate Ib or its salt or adduct to iminoctadine II or its salt or adduct is 10:1 to 0.05:2.

3. The composition defined in claim 1 which is conditioned in two parts, one part comprising the carbamate Ib or its salt or adduct in a solid or liquid carrier, and the other part comprising iminoctadine II or its salt or adduct in a solid or liquid carrier.

4. The composition defined in claim 1, further comprising an oxime ether Ia (Ia)

or a salt or adduct thereof.

5. The composition defined in claim 4, wherein the weight ratio of the carbamate Ib or its salt or adduct to iminoctadine II or its salt or adduct is 10:1 to 0.05:2.

6. The composition defined in claim 4, wherein the weight ratio of the oxime ether Ia or its salt or adduct to iminoctadine II or its salt or adduct is 10:1 to 0.05:2.

7. The composition defined in claim 4 which is conditioned in two parts, one part comprising the carbamate Ib or its salt or adduct and the oxime ether Ia or its salt or adduct in a solid or liquid carrier, and the other part comprising iminoctadine II or its salt or adduct in a solid or liquid carrier.

8. A method of controlling harmful fungi, which comprises treating the harmful fungi, their environment, or the plants, seeds, soils, areas, materials or spaces to be kept free from said fungi with synergistically effective amounts of a carbamate Ib or a salt or adduct thereof and iminoctadine II or a salt or adduct thereof as defined in claim 1.

9. The method of claim 8, wherein the carbamate Ib or its salt or adduct and iminoctadine II or its salt or adduct are applied simultaneously together or separately, or in succession.

10. The method of claim 8, wherein the carbamate Ib or its salt or adduct is applied at a rate of from 0.01 to 2.5 kg/ha.

11. The method of claim 8, wherein iminoctadine II or its salt or adduct is applied at a rate of from 0.01 to 5 kg/ha.

12. The method of claim 8, further comprising treating the harmful fungi, their environment, or the plants, seeds, soils, areas, materials or spaces to be kept free from said fungi with a synergistically effective amount of an oxime ether Ia

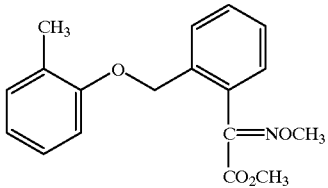

(Ia)

or a salt or adduct thereof.

13. The method defined in claim 12, wherein the carbamate Ib or its salt or adduct and iminoctadine II or its salt or adduct are applied simultaneously together or separately, or in succession.

14. The method defined in claim 12, wherein the oxime ether Ia or its salt or adduct and iminoctadine II or its salt or adduct are applied simultaneously together or separately, or in succession.

15. The method of claim 12, wherein the carbamate Ib or its salt or adduct is applied at a rate of from 0.01 to 2.5 kg/ha.

16. The method of claim 12, wherein the oxime ether Ia or its salt or adduct is applied at a rate of from 0.01 to 2.5 kg/ha.

17. The method of claim 12, wherein iminoctadine II or its salt or adduct is applied at a rate of from 0.01 to 5 kg/ha.

* * * * *

UNITED STATES PATENT AND TRADEMARK OFFICE
CERTIFICATE OF CORRECTION

PATENT NO.: 6,166,058

DATED: December 26, 2000

INVENTOR(S): MUELLER et al.

It is certified that error appears in the above-identified patent and that said Letters Patent is hereby corrected as shown below:

Col. 6, claim 1, line 33, before "iminoctadine II" insert --b)    --.

Signed and Sealed this

First Day of May, 2001

NICHOLAS P. GODICI

Attest:

Attesting Officer    Acting Director of the United States Patent and Trademark Office